(12) United States Patent
LeBoeuf et al.

(10) Patent No.: US 12,014,830 B2
(45) Date of Patent: Jun. 18, 2024

(54) SYSTEM AND METHOD FOR AUTOMATION OF SURGICAL PATHOLOGY PROCESSES USING ARTIFICIAL INTELLIGENCE

(71) Applicant: Mary Hitchcock Memorial Hospital, for itself and on behalf of Dartmouth-Hitchcock Clinic, Lebanon, NH (US)

(72) Inventors: Matthew LeBoeuf, Hanover, NH (US); Joshua J. Levy, Lebanon, NH (US); Louis J. Vaickus, Etna, NH (US)

(73) Assignee: Mary Hitchcock Memorial Hospital, for itself and on behalf of Dartmouth-Hitchcock Clinic, Lebanon, NH (US)

( * ) Notice: Subject to any disclaimer, the term of this patent is extended or adjusted under 35 U.S.C. 154(b) by 241 days.

(21) Appl. No.: 17/722,567

(22) Filed: Apr. 18, 2022

(65) Prior Publication Data
US 2022/0375604 A1   Nov. 24, 2022

Related U.S. Application Data

(60) Provisional application No. 63/176,333, filed on Apr. 18, 2021.

(51) Int. Cl.
G16H 50/20 (2018.01)
G16H 15/00 (2018.01)
(Continued)

(52) U.S. Cl.
CPC .......... *G16H 50/20* (2018.01); *G16H 15/00* (2018.01); *G16H 30/40* (2018.01); *G16H 70/60* (2018.01)

(58) Field of Classification Search
CPC ........ G16H 50/20; G16H 70/60; G16H 15/00; G16H 30/40
See application file for complete search history.

(56) References Cited

U.S. PATENT DOCUMENTS 3,975,762 A * 8/1976 van den Bosch ........ H04N 9/43
348/32
5,075,214 A * 12/1991 Connor .................... C12Q 1/70
435/5
(Continued)

FOREIGN PATENT DOCUMENTS

WO    2020180755    9/2020

OTHER PUBLICATIONS

Akbar, 2019, Scientific Reports, pp. 1-9.*
(Continued)

*Primary Examiner* — Michael I Ezewoko
(74) *Attorney, Agent, or Firm* — Loginov & Associates, PLLC; William A. Loginov

(57) ABSTRACT

This invention provides a system for automation of a pathology process, which includes a processor having trained artificial intelligence (AI) modules operating in association therewith, adapted to receive image data from camera images of whole tissue acquired by a camera assembly and whole slide images (WSIs) of inked and segmented tissue samples. A mask produces image results for tissue with holes and free of holes, and a filter provides filtered image results to the AI modules, detecting tumors and macroarchitecture features. A quality assessment process produces quality score outputs for tumors and macroarchitecture features. A report generator provides reports with one or more parameters to a user via an interface. More particularly, the report generator automatically creates a pathology report, having a written description and pictorial diagram relative to the (Continued)

gross images of the tissue integrating the outputs of the AI modules used to analyze the whole slide digital images.

17 Claims, 13 Drawing Sheets

(51) Int. Cl.
*G16H 30/40* (2018.01)
*G16H 70/60* (2018.01)

(56) References Cited

U.S. PATENT DOCUMENTS

| | | | | |
|---|---|---|---|---|
| 5,218,529 | A * | 6/1993 | Meyer | G06N 3/02 706/924 |
| 5,544,650 | A * | 8/1996 | Boon | G06N 3/04 382/133 |
| 5,784,162 | A * | 7/1998 | Cabib | G01J 3/453 435/6.12 |
| 5,976,885 | A * | 11/1999 | Cohenford | G01J 3/453 436/171 |
| 5,991,028 | A * | 11/1999 | Cabib | G06V 20/69 382/133 |
| 6,146,897 | A * | 11/2000 | Cohenford | G01J 3/453 436/171 |
| 6,463,438 | B1 * | 10/2002 | Veltri | G06V 20/695 706/15 |
| 6,690,817 | B1 * | 2/2004 | Cabib | G01N 33/582 382/165 |
| 7,693,334 | B2 * | 4/2010 | Ogura | G06F 18/211 382/128 |
| 8,351,676 | B2 * | 1/2013 | Dai | G06V 20/698 382/128 |
| 9,518,982 | B2 * | 12/2016 | Sood | G01N 33/582 |
| 9,786,050 | B2 * | 10/2017 | Bhargava | G06V 20/69 |
| 9,983,195 | B2 * | 5/2018 | King | G01N 33/5011 |
| 10,013,760 | B2 * | 7/2018 | Bhargava | G06T 7/0014 |
| 10,013,781 | B1 * | 7/2018 | Gammage | G06N 5/047 |
| 10,521,901 | B2 * | 12/2019 | Ikemoto | G06T 7/0012 |
| 10,935,773 | B2 * | 3/2021 | Johnson | G02B 21/008 |
| 11,504,103 | B2 * | 11/2022 | Johnson | A61B 18/1482 |
| 11,508,045 | B1 * | 11/2022 | Amthor | G06T 5/20 |
| 11,526,984 | B2 * | 12/2022 | Barnes | G06T 7/0012 |
| 11,614,610 | B2 * | 3/2023 | Johnson | G01N 15/1429 382/128 |
| 11,620,751 | B2 * | 4/2023 | Sarkar | G06T 7/90 382/103 |
| 11,621,058 | B2 * | 4/2023 | Gurcan | G06N 3/047 702/19 |
| 11,631,171 | B2 * | 4/2023 | Leng | G16H 30/40 702/19 |
| 11,633,146 | B2 * | 4/2023 | Leng | G16H 30/20 600/423 |
| 11,672,425 | B2 * | 6/2023 | Pyun | G01J 3/0218 600/477 |
| 11,675,178 | B2 * | 6/2023 | Wirch | G02B 21/26 382/226 |
| 11,681,418 | B2 * | 6/2023 | Wirch | G06V 10/7788 382/128 |
| 11,684,264 | B2 * | 6/2023 | Bryant-Greenwood | G06T 5/90 600/407 |
| 11,751,903 | B2 * | 9/2023 | Knowlton | A61B 90/02 604/22 |
| 11,751,904 | B2 * | 9/2023 | Knowlton | A61B 17/32093 604/22 |
| 11,759,231 | B2 * | 9/2023 | Knowlton | A61B 18/14 604/22 |
| 11,776,124 | B1 * | 10/2023 | Behrooz | G06T 7/0014 382/128 |
| 11,776,681 | B2 * | 10/2023 | Godrich | G16H 40/20 382/128 |
| 11,783,603 | B2 * | 10/2023 | Stumpe | G06F 18/214 |
| 2001/0018659 | A1 * | 8/2001 | Koritzinsky | A61B 6/56 705/3 |
| 2003/0026762 | A1 * | 2/2003 | Malmros | A61K 49/003 424/9.6 |
| 2006/0210153 | A1 * | 9/2006 | Sara | G01J 3/46 382/165 |
| 2007/0127022 | A1 * | 6/2007 | Cohen | G01N 21/65 356/326 |
| 2007/0135999 | A1 * | 6/2007 | Kolatt | G06V 20/695 702/19 |
| 2008/0015448 | A1 * | 1/2008 | Keely | A61B 5/0068 600/562 |
| 2008/0166035 | A1 * | 7/2008 | Qian | G06V 20/698 382/133 |
| 2008/0273199 | A1 * | 11/2008 | Maier | G01J 3/0291 356/301 |
| 2008/0319324 | A1 * | 12/2008 | Maier | G01J 3/02 600/477 |
| 2009/0002702 | A1 * | 1/2009 | Maier | A61B 5/7264 702/19 |
| 2009/0024375 | A1 * | 1/2009 | Kremer | G16B 15/10 703/11 |
| 2009/0319291 | A1 * | 12/2009 | Noordvyk | G16H 50/20 705/2 |
| 2011/0080581 | A1 * | 4/2011 | Bhargava | G01J 3/02 356/302 |
| 2011/0182490 | A1 * | 7/2011 | Hoyt | G06V 20/698 382/128 |
| 2011/0286654 | A1 * | 11/2011 | Krishnan | G06T 7/155 382/128 |
| 2012/0034647 | A1 * | 2/2012 | Herzog | G01N 33/49 435/288.7 |
| 2012/0052063 | A1 * | 3/2012 | Bhargava | G06F 18/2415 382/128 |
| 2012/0092663 | A1 * | 4/2012 | Kull | G01N 21/65 356/244 |
| 2012/0143082 | A1 * | 6/2012 | Notingher | G01N 21/65 600/562 |
| 2012/0200694 | A1 * | 8/2012 | Garsha | G01N 21/6456 382/128 |
| 2012/0212733 | A1 * | 8/2012 | Kodali | G01N 21/658 977/773 |
| 2012/0226644 | A1 * | 9/2012 | Jin | G06N 3/045 706/19 |
| 2012/0290607 | A1 * | 11/2012 | Bhargava | G16H 50/70 707/769 |
| 2013/0022250 | A1 * | 1/2013 | Nygaard | G01N 21/359 382/128 |
| 2014/0235487 | A1 * | 8/2014 | McDevitt | G16H 50/30 702/19 |
| 2014/0270457 | A1 * | 9/2014 | Bhargava | G06V 20/69 382/133 |
| 2014/0336261 | A1 * | 11/2014 | Chin | A61P 35/00 514/604 |
| 2015/0268226 | A1 * | 9/2015 | Bhargava | G01N 33/5091 514/789 |
| 2015/0374306 | A1 * | 12/2015 | Gelbman | G06V 40/171 600/476 |
| 2016/0042511 | A1 * | 2/2016 | Chukka | G06V 20/695 382/133 |
| 2016/0272934 | A1 * | 9/2016 | Chander | C12M 47/04 |
| 2016/0335478 | A1 * | 11/2016 | Bredno | A61B 34/74 |
| 2017/0160171 | A1 * | 6/2017 | Tsujikawa | G01N 1/44 |
| 2017/0169567 | A1 * | 6/2017 | Chefd'hotel | G06T 7/0012 |
| 2017/0322124 | A1 * | 11/2017 | Barnes | G06T 7/0014 |
| 2017/0358082 | A1 * | 12/2017 | Bhargava | G06V 20/69 |
| 2017/0372471 | A1 * | 12/2017 | Eurèn | G06F 18/214 |
| 2018/0232883 | A1 * | 8/2018 | Sethi | G16H 30/40 |
| 2019/0188446 | A1 * | 6/2019 | Wu | G06V 20/695 |
| 2020/0302603 | A1 * | 9/2020 | Barnes | G06T 7/0012 |
| 2020/0372235 | A1 * | 11/2020 | Peng | G06V 20/695 |
| 2020/0372635 | A1 | 11/2020 | Veidman | |
| 2020/0394825 | A1 * | 12/2020 | Stumpe | G06V 10/82 |
| 2021/0103797 | A1 | 4/2021 | Jang | |
| 2021/0295507 | A1 * | 9/2021 | Nie | G06T 7/0012 |
| 2022/0146418 | A1 * | 5/2022 | Bauer | G01N 21/35 |

(56) References Cited

U.S. PATENT DOCUMENTS

2023/0249175 A1\* 8/2023 Linnes ................. B01L 3/5027
                                                        435/6.12
2023/0279512 A1\* 9/2023 Masters ............ B01L 3/502761
                                                        435/5
2023/0394716 A1\* 12/2023 de Haan ................ G06V 20/69

OTHER PUBLICATIONS

Arunachalam, 2019, PLOS ONE, pp. 1-19.\*
Corvo, 2017 IEEE Workshop on Visual Analytics in Healthcare, pp. 77-83.\*
McCann, IEEE Signal Processing Magazine, 2015, pp. 78-87.\*
Rivenson, 2020, BMEF, pp. 1-11.\*
Taieb, 2019, ArXiv, pp. 1-58.\*
Grala, 2009, pp. 587-592.\*
U.S. Appl. No. 16/679,133, entitled System and Method for Analyzing Cytological Tissue Preparations, Louis J. Vaickus, filed Nov. 8, 2018.

\* cited by examiner

FIG. 1 df_hole_quality_score —952

| index | section_1 | section_2 | section_3 |
|---|---|---|---|
| dermis | 1.905518 | 8.697915 | 5.635551 |
| epidermis | 0.205924 | 0.368982 | 0.862641 |
| subcutaneous tissue | 0.556756 | 4.231215 | 3.011801 | df_tumor_quality_score —954

| index | section_1 | section_2 | section_3 |
|---|---|---|---|
| dermis | 0.044323 | 0.142002 | 0.019765 |
| hole | 0.088639 | 0.008829 | 0.022807 |
| subcutaneous tissue | 0.034402 | 0.055307 | 0.023350 |

SYSTEM AND METHOD FOR AUTOMATION OF SURGICAL PATHOLOGY PROCESSES USING ARTIFICIAL INTELLIGENCE

RELATED APPLICATION

This application claims the benefit of co-pending U.S. Provisional Application Ser. No. 63/176,333, entitled SYSTEM AND METHOD FOR AUTOMATION OF SURGICAL PATHOLOGY PROCESSES USING ARTIFICIAL INTELLIGENCE, filed Apr. 18, 2021, the teachings of which are expressly incorporated herein by reference.

FIELD OF THE INVENTION

This invention relates to pathology systems and methods that employ automated processes, and more particularly to tissue slide analysis.

BACKGROUND OF THE INVENTION

Measurement of tissue size, determination of grossing approach, and tissue inking are all currently performed manually by highly reimbursed specialized histotechnicians, physician assistants, or pathology residents. Analysis of tissue quality is performed by the pathologists but is not reflected in the pathology report and because of its subjective nature results in significant variation.

Following the resection of solid tumors, the tissue is removed and (a) measured, (b) processed, (c) grossed, (d) inked, (e) sectioned, (f) stained, (g) slides read by a pathologist, (h) pathology report is created. By way of background, a typical pathology report 100 is shown in FIG. 1. This exemplary report 100 provides a Diagnosis section 100, the Specimens Submitted 112 (e.g. location on the body), Clinical Information 114, and Specimen Processing details 116 related to (e.g.) quantity and size, tissue description, inking, etc. In a current implementation, each of steps (a)-(h) are typically performed manually, and there are no standardized quality control mechanisms in place outside of the pathologist reading the slides to ensure that high quality tissue is available to the pathologist and automated reagent checks in processors and autostainers (which do not directly assess tissue quality). This process occurs hundreds of thousands of times per year in surgical pathology laboratories across the United States, requiring significant manual input from staff. Whole slide imaging is becoming a more commonly accepted method to digitize the slides allowing subsequent interpretation by the pathologist. Digitization of slides has allowed the field of pathology to start developing and integrating machine learning and artificial intelligence approaches to act as diagnostic aids for the pathologist. The majority of research and efforts currently are focused around clinical diagnosis however in addition to diagnosis there are tissue characteristics that must be taken into account. Additionally, these machine learning and AI approaches are aimed at increasing the efficiency of the pathologist, however digitized efforts have not focused on the upstream process from removed tissue to digitized slide, only on the quality and speed of scanning.

FIG. 1A hence shows, an arrangement 101 that is part of an automated slide scanning and analysis system and method, such as shown in commonly assigned U.S. patent application Ser. No. 16/679,133, entitled SYSTEM AND METHOD FOR ANALYZING CYTOLOGICAL TISSUE PREPARATIONS, filed Nov. 8, 2018, the teachings of which are incorporated by reference. The depicted arrangement 101 provides a user-based microscopic analysis system/device 111, that includes an image acquisition module of known construction, including an imaging sensor S that can convert received light, via magnifying optics O, from a slide or other surface 113 containing a tissue sample or other smear of cellular matter 115, that can be prepared using conventional cytological techniques and substances from a human or animal subject. Note that the sensor S can be part of a generalized "camera" or "camera assembly" that also includes optics O, and which should be taken broadly to mean any mechanism that can convert an imaged scene into image data define (e.g.) in the form of black and white or color pixels of a given array (e.g. N×M) size. The acquired, magnified image data 120 is stored and/or transmitted over a network (e.g. the Internet and/or a WAN/LAN) to a computing system 130 that can be instantiated in one or more servers and/or a cloud environment. The server/cloud system 130 includes one or more processors (that can be local and/or distributed 140, and associated data storage (that can be local and/or distributed) 150. As described below, the data 150 can consist of training data, based upon prior images and associated diagnosis. Other data can also be stored as appropriate to carry out the functions of the system and method. The processor(s) 140 carry out an associated image process 160 that can include the various functional modules described hereinbelow. One exemplary module includes vision tools 162, which can be a variety of edge detectors, color analyzers, blob analyzers and other commercially available machine vision applications used to resolve objects within an image and apply pattern recognition thereto. The process(or) 160 further includes a neural net/deep learning-based training process(or) 164 that carries out various training tasks and steps as described below, including the identification and classification of expert-based image data on various cell conditions in an overall library of cell images. Additionally, the process(or) 160 includes a neural net/deep learning-based runtime process (or) 166 that applies the training data and associated classifiers to the acquired image data of a slide 112 to determine associated diagnostic data. A user interface device 170, in the form of a computer, having a screen/touchscreen 172, keyboard 174, mouse 176, etc. is shown linked to the server/cloud 130 via an appropriate network, such as the Internet, LAN or WAN. This device 170 can be any acceptable data handling appliance, such as a smartphone, tablet, laptop, PC or server, and is capable of manipulating (e.g.) web page information that can be used to communicate with the cloud/server and associated processes/modules. This device 170 can be one of many, used by clinicians and other interested parties, who desire to obtain diagnostic data from the system and method. The computing/interface device 170 can also facilitate upload of local image data 180 of slides via a link 182 with the microscope/acquisition device 111.

It is generally desirable to use machine learning and artificial intelligence to automate the routine but very necessary parts of the surgical pathology report while significantly improving efficiency of the surgical pathology lab thereby reducing turnaround time and decreasing cost while increasing quality.

Tissue Size

Recording tissue size is a critical piece of information in the pathology report. Tissue size dictates how the piece of tissue is grossed in terms of the number of tissue blocks and cassettes that are needed to adequately assess the tissue. The number of cassettes and subsequent slides per cassette influence the amount of total tissue that is analyzed by the pathologist and the amount of time that is required to produce and read the slides. This is a balance. Currently the amount of tissue analyzed (compared to the total volume of tissue removed) is not well reflected in the pathology report. If insufficient tissue is analyzed serious adverse consequences can occur, for instance, a false negative margin resulting in tumor recurrence in the future. Therefore maximizing the amount of tissue that can be placed into a cassette/onto a slide in an efficient manner decreases the number of required cassettes while increasing the proportion of tissue analyzed. This results in an overall increase in efficiency, and a more regimented, reproducible process. Note that in the report 100 of FIG. 1 there are a total of 10 cassettes utilized in the grossing of the tissue resulting (see box 117 in FIG. 1), can be decreased by knowing the optimal grossing and inking scheme which are dependent on accurately calculating the size of the piece of tissue removed. Additionally, accurate calculation of the piece of tissue removed will aid in quantifying the percentage of margin analyzed by the pathologist and develop a body of quantitative body of data that can inform more advanced prognostication.

1. Tissue Inking

Tissue ink is used for at least purposes, namely (a) to orient the tissue, and (b) to define whether all of the tissue is contained within the tissue section, i.e. there is not any tissue missing and ink spans the complete border of the tissue. Orientation of the tissue is required when evaluating specimen margins either in real-time (from the operating room (OR), or in Mohs Surgery), or post-operatively when tissue is being analyzed in the event that there is tumor at the margin which would require additional treatment. See the diagram 200 of an exemplary procedure in FIG. 2 in which the tissue sample 210 is divided into quarters 212, and such is diagrammed/mapped 214 by the practitioner. An exemplary, detailed diagram 220 with notations regarding the excision site, and associated features is also shown. Tissue inking is also used to map the tumor, so as to allow planning of additional removal. Currently, there is no standardization across institutions, or mandate by regulatory agencies (CAP, AJCC) regarding the grossing and inking process, and the ink colors are interpreted by the pathologist (typically according to institutional norms). Notably, current tissue mapping and ink interpretation is performed manually, which takes time and creates the possibility for error, particularly in situations when the individual inking the tissue and pathologists reading the slides are different (which is virtually universally the case in modern, sub-specialized pathology labs).

2. Slide Quality

The ability to make an accurate histologic diagnosis or fully identify tissue margins for the presence or absence of a tumor relies on the high quality tissue sections (a very commonly overlooked factor, even for experienced pathologists). Holes or defects (e.g. hole/nick 210 in FIG. 2) in the tissue can represent areas where tumor has fallen out during tissue processing and must be recognized and taken into account by the pathologists. Production of high quality tissue sections is not trivial and can vary based on the type of tissue processing (frozen versus permanent section). Currently, slides are read by pathologists however there is no standardized method to report tissue section quality, beyond reporting on processing issues such as understaining and blade chatter. This is particularly relevant when working with fresh frozen tissue as the ability to obtain complete tissue sections can be challenging based on the nature of the tissue, for example, tissue containing significant fat components can be more challenging to cut/excise without (free of) tearing. However, the ability to use fresh frozen tissue for analysis tasks allows for real-time diagnosis or margin analysis allowing for improved patient care by decreasing the need for additional procedures (the so-called intraoperative frozen section). This also has significant cost benefits as it eliminates the need for tissue fixation, transport, and processing, all of which involve significant labor and include the use of toxic chemicals which must be both handled in special areas and then disposed of in a safe manner. In addition, to quality, quantifying the amount of tissue analyzed may provide important information in instances where tumor recurrence occurs or there are downstream pathologic questions.

FIG. 3 shows inked tissue samples, by way of example, in which holes 310 are outlined in (e.g.) brown. Other features, such as tumor features 320 are outlined as shown, and described further below. Entry of information pertaining to tissue size and appearance, grossing, and inking are all manually inputted into the system by highly reimbursed specialists including histotechnicians and physician assistants. The repetitive nature of the surgical pathology lab make it desirable in an optimal setting to automate processes through the use of artificial intelligence and indeed very simple improvements such as keyboard shortcuts and voice dictation are very well received and have been shown to improve efficiency and reduce errors.

SUMMARY OF THE INVENTION

This invention overcomes disadvantages of the prior art by providing a system and method that effectively automates the early/preliminary and vital part of the overall pathology procedure that is typically repetitive and labor intensive and fundamentally determines which tissue is actually provided to diagnostic slides used by downstream pathologists and other practitioners in treatment of a condition, such as but not limited to skin cancer. These tools, including ink recognition, can provide additional information to the pathologist when analyzing digital pathology images. Significantly, this system and method aids in supporting a vital practice guideline, which is to avoid a diagnosis without sufficient information. This system organizes automated input and output data as above to generate a pathology report that can be efficiently and clearly interpreted.

In an illustrative embodiment, a system and method for automation of a pathology process is provided, which includes a processor having trained artificial intelligence (AI) modules operating in association therewith, adapted to receive image data from camera images of whole tissue acquired by an camera assembly and whole slide images (WSIs) of inked and segmented tissue samples. A mask produces image results for tissue with holes and free of holes, and a filter provides filtered image results to the AI modules, which thereby detects tumors and macroarchitecture features. A quality assessment process produces quality score outputs for tumors and macroarchitecture features. A report generator then provides reports with one or more parameters to a user via an interface. More particularly, the report generator automatically creates a pathology report consisting of a written description and pictorial diagram relative the images of the tissue. Illustratively, a tissue determination process can determine a size and a description of tissue automatically based upon characteristics in the images acquired by the camera assembly. Additionally, a tissue grossing and inking process can automatically generate a grossing and inking scheme based upon a user input of desired percentage of tissue margins analyzed and the tissue size. The AI modules can include a tumor inflammation convolutional neural network (CNN), a macroarchitecture hole CNN, a tumor detection graphical neural network (GNN) and a macroarchitecture detection GNN. Additionally, the filters can include at least one of a Sobel filter and a gradient-based filter. An ink detection and orientation process can operate on the filtered images of the tissue samples and delivers results thereof to the report generator. The report generator can receive results from a quality assessment process acting on results from the a tumor detection GNN and a macroarchitecture detection GNN. Illustratively, the macroarchitecture can be defined by at least one of holes, fat, edges, dermis and epidermis information. A visual generation and 3D stitching process can provide results to the report generator, and can receive information from a cell nuclei detection process. Outputs of the aforementioned CNN/GNNs are thereby used to automatically generate a pathology report.

BRIEF DESCRIPTION OF THE DRAWINGS

The invention description below refers to the accompanying drawings, of which:

FIG. 1 is a diagram showing a typical surgical pathology report of interest in association with the system and method according to embodiments herein;

FIG. 9A is an exemplary printout of the numerical scores according to the graph of FIG. 9.

DETAILED DESCRIPTION

Figure 1:
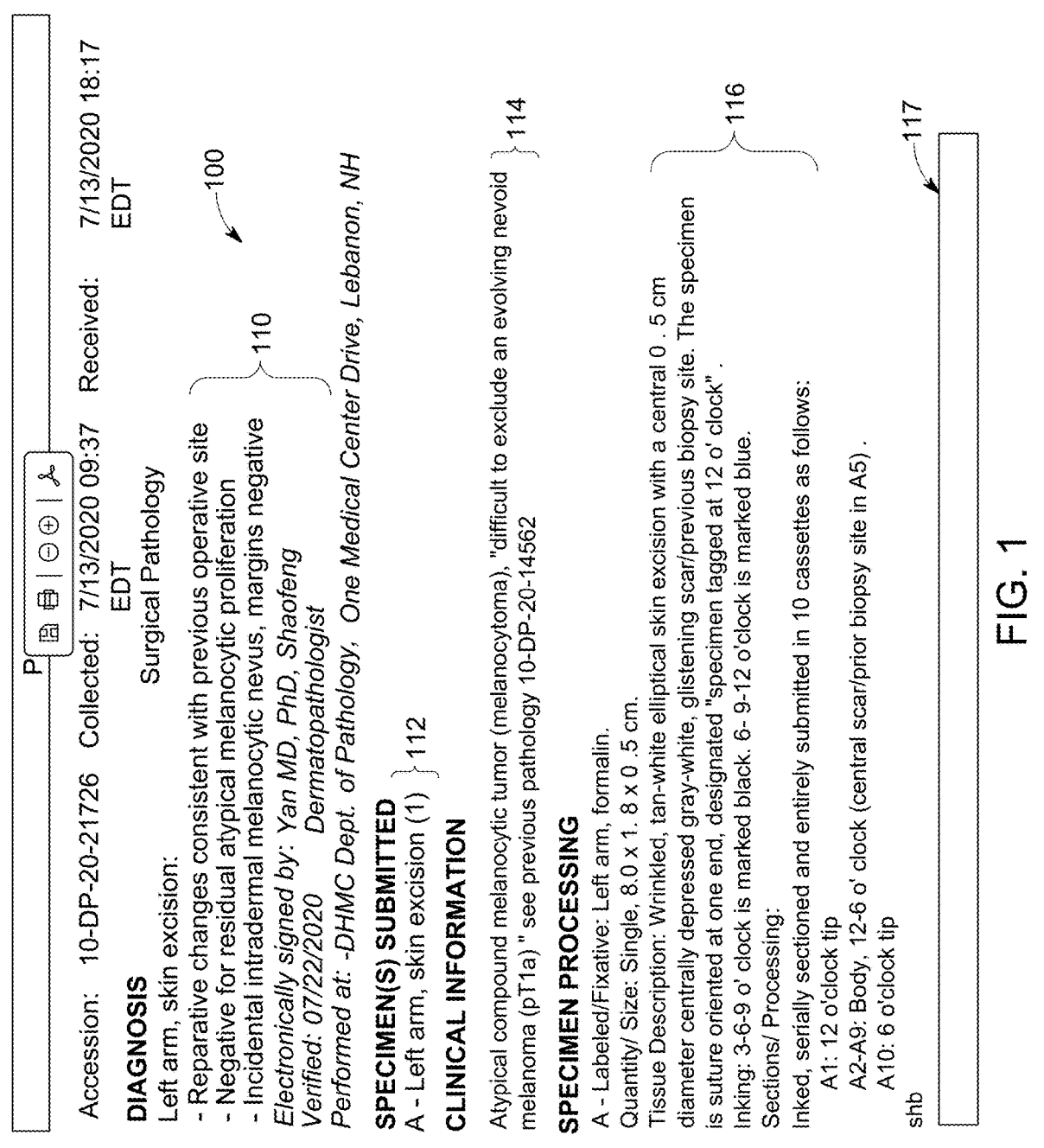
Figure 1A:
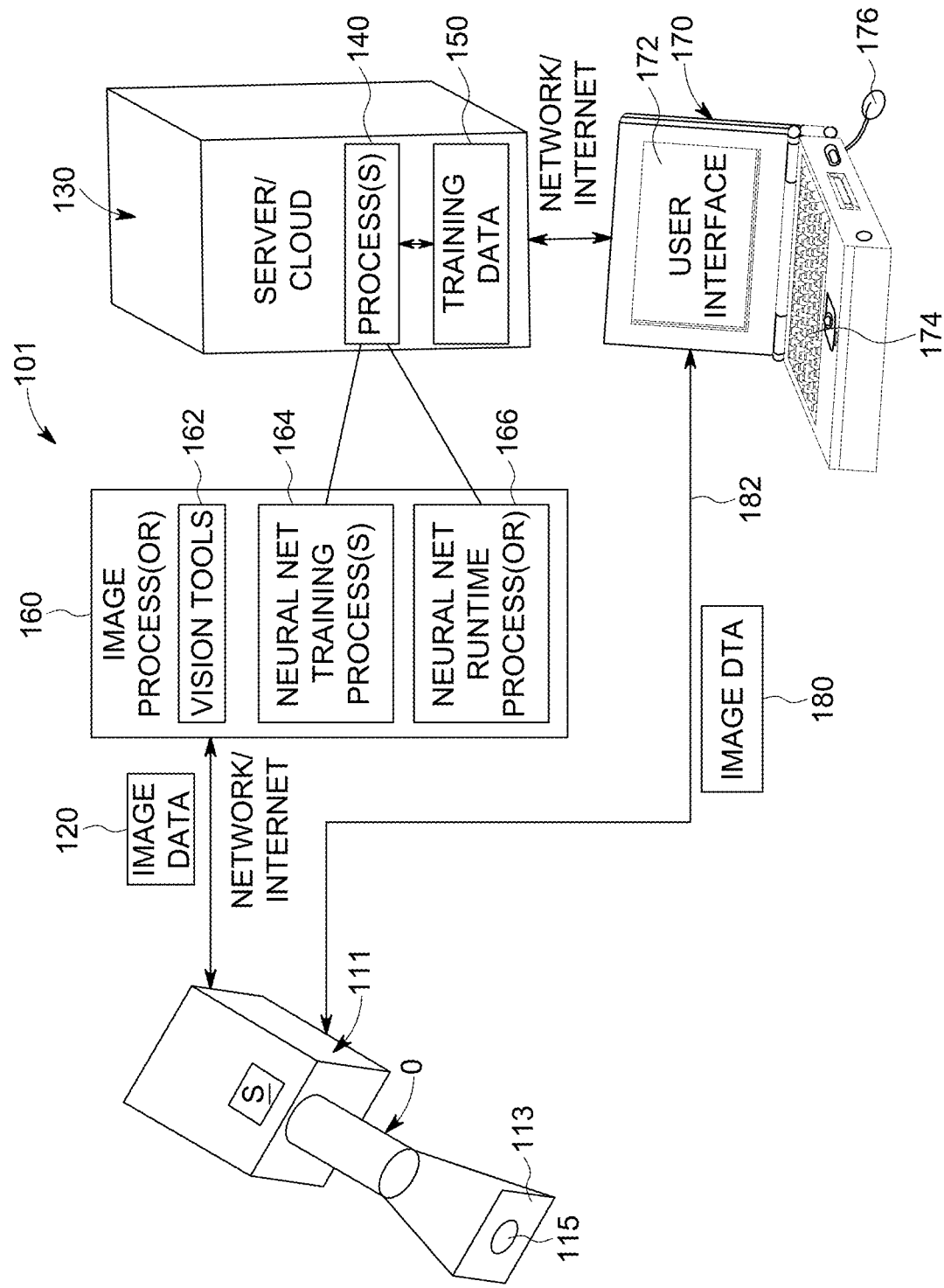
FIG. 1A is an exemplary, generalized computing arrangement including an artificial intelligence process and associated data-handling processes/modules for use with the system and method herein.
Figure 2:
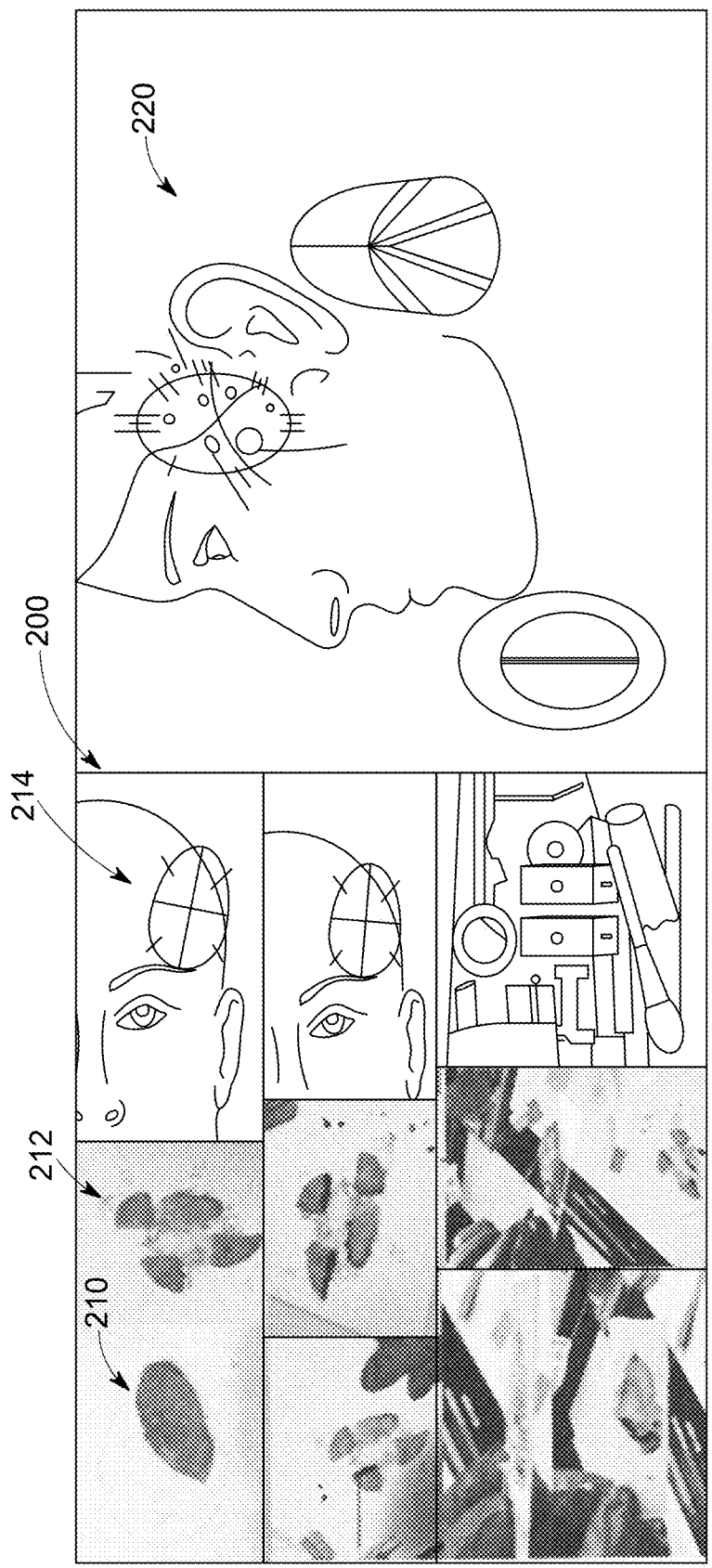
FIG. 2 is a diagram showing an exemplary of tissue grossing, inking, mounting, and mapping process.
Figure 3:
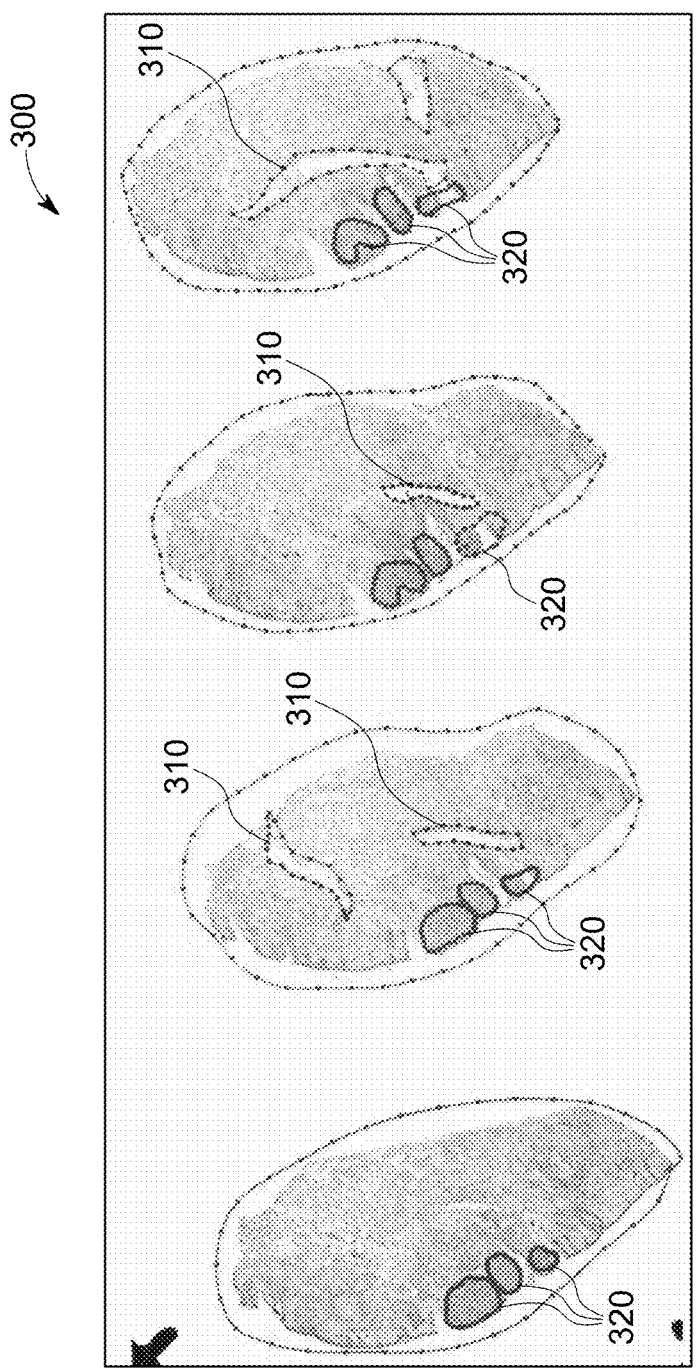
FIG. 3 is diagram showing a series of images of exemplary tissue sections with holes outlined thereon.

With further reference to the generalized computing environment described in FIG. 1A above, a system and method for automation of surgical processes using artificial intelligence and/or deep learning is now described.

1. Tissue Size

Figure 4:
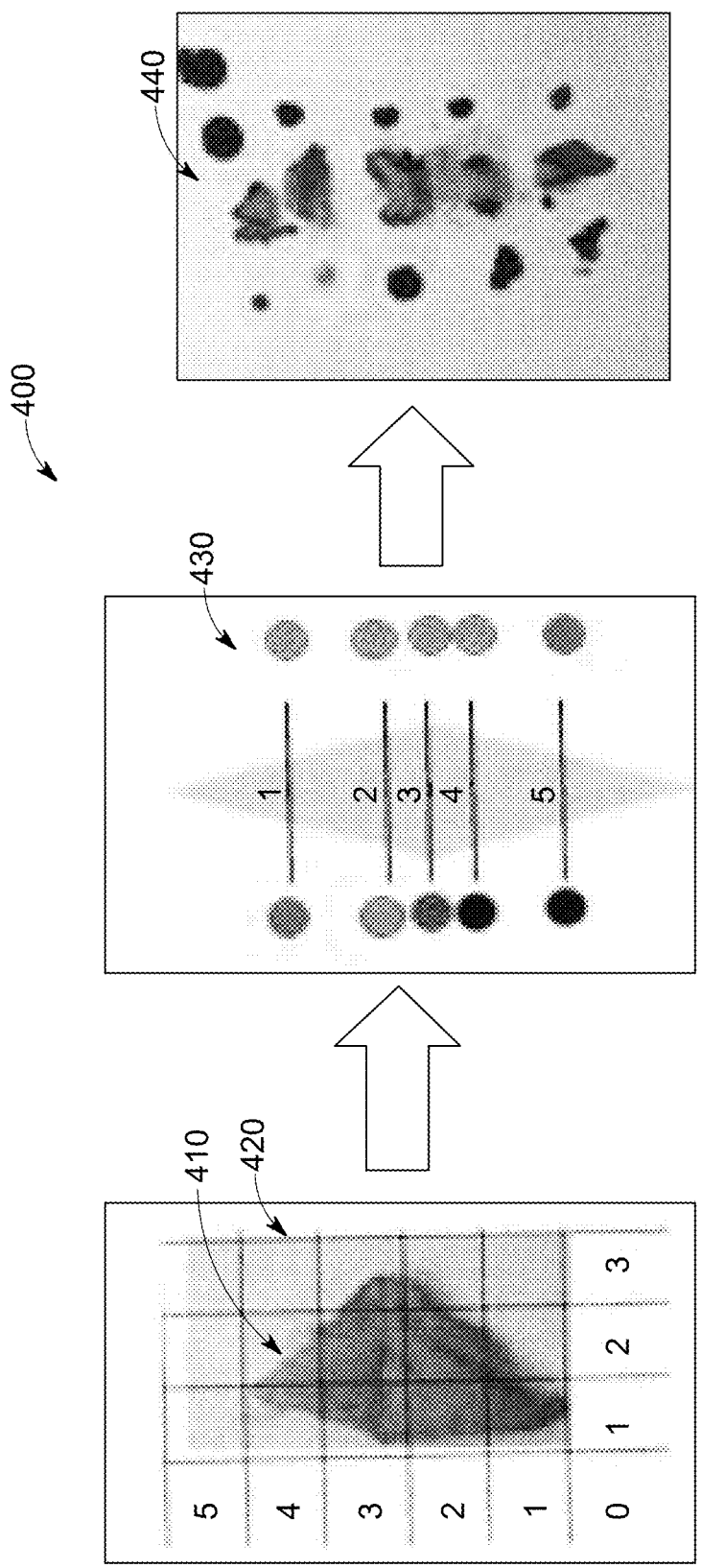
FIG. 4 is a flow diagram showing a generalized procedure for automation of tissue size, appearance description and grossing.

With reference to the flow diagram 400 of FIG. 4, images of tissue 410 are captured on a defined grid 420, and photographed from a standard distance. This is used to (a) calculate tissue size (length×width), (b) volume added in 3-D if necessary via trapezoid, and (c) B-spline fitting between serial sections of detected tissue. Additionally, an image recognition feature is used to define the gross appearance of the tissue—for example a "tan ellipse with central biopsy site". A schematic 430 of the tissue sample is shown and individual features 440 are broken out based upon inking. The tissue size can be used to define a grossing and inking scheme that will subsequently as defined below inform the exact piece of tissue on the slide. Note that normally this specimen would be grossed and placed into e.g. five (5) different cassettes. In this example the case can be placed entirely into less cassettes. As the size of the tissue increases this can be significant important to maximize efficiency in the surgical pathology laboratory and reduce the chance of error. The predefined inking system will be interpreted histologically as per the tissue ink detection described below. This technology can be applied to any solid tissue.

2. Tissue Orientation via Ink Detection System

Figure 5:
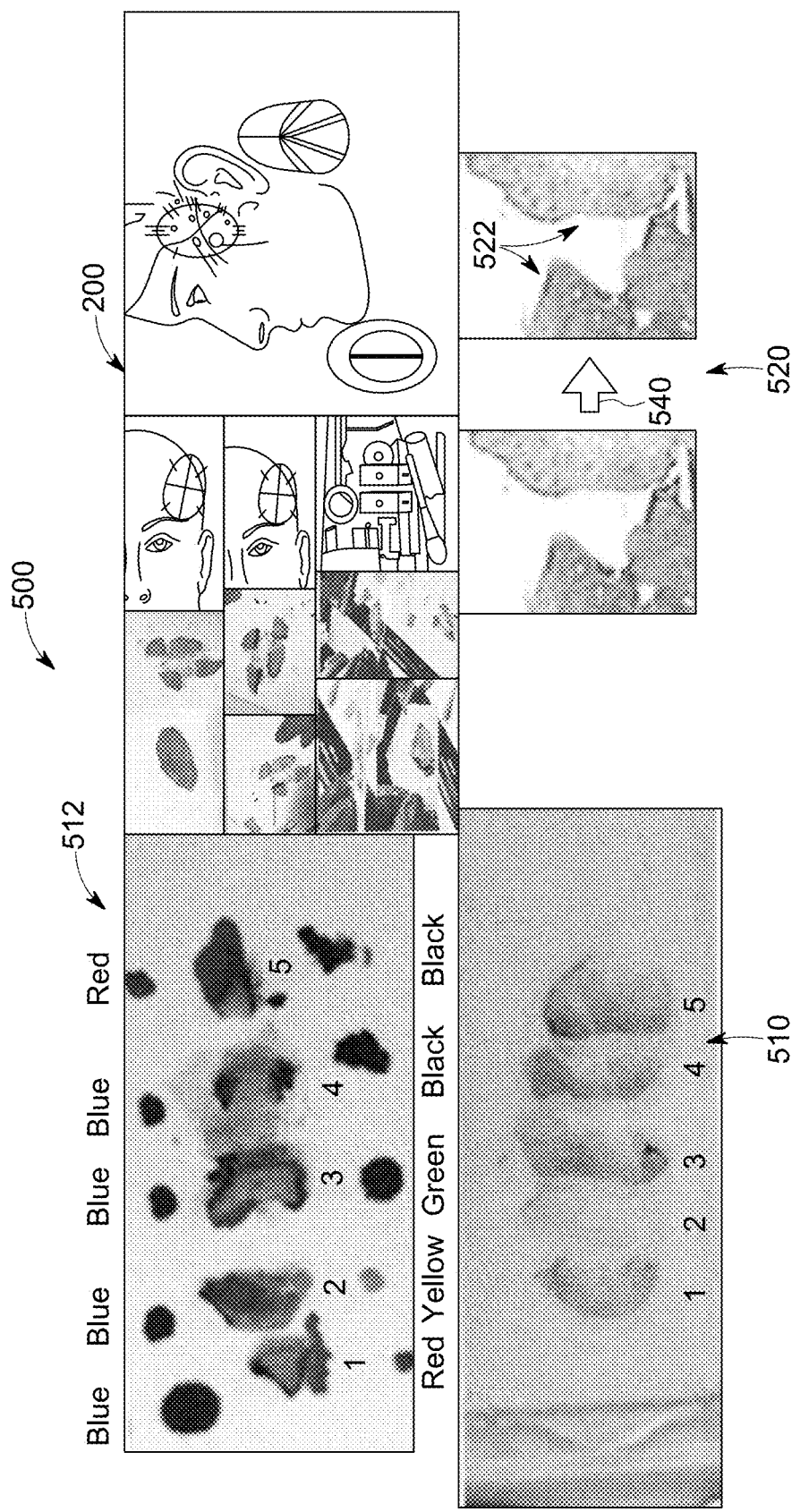
FIG. 5 is a diagram showing an overview of inking scheme and associated procedures.
Figure 6:
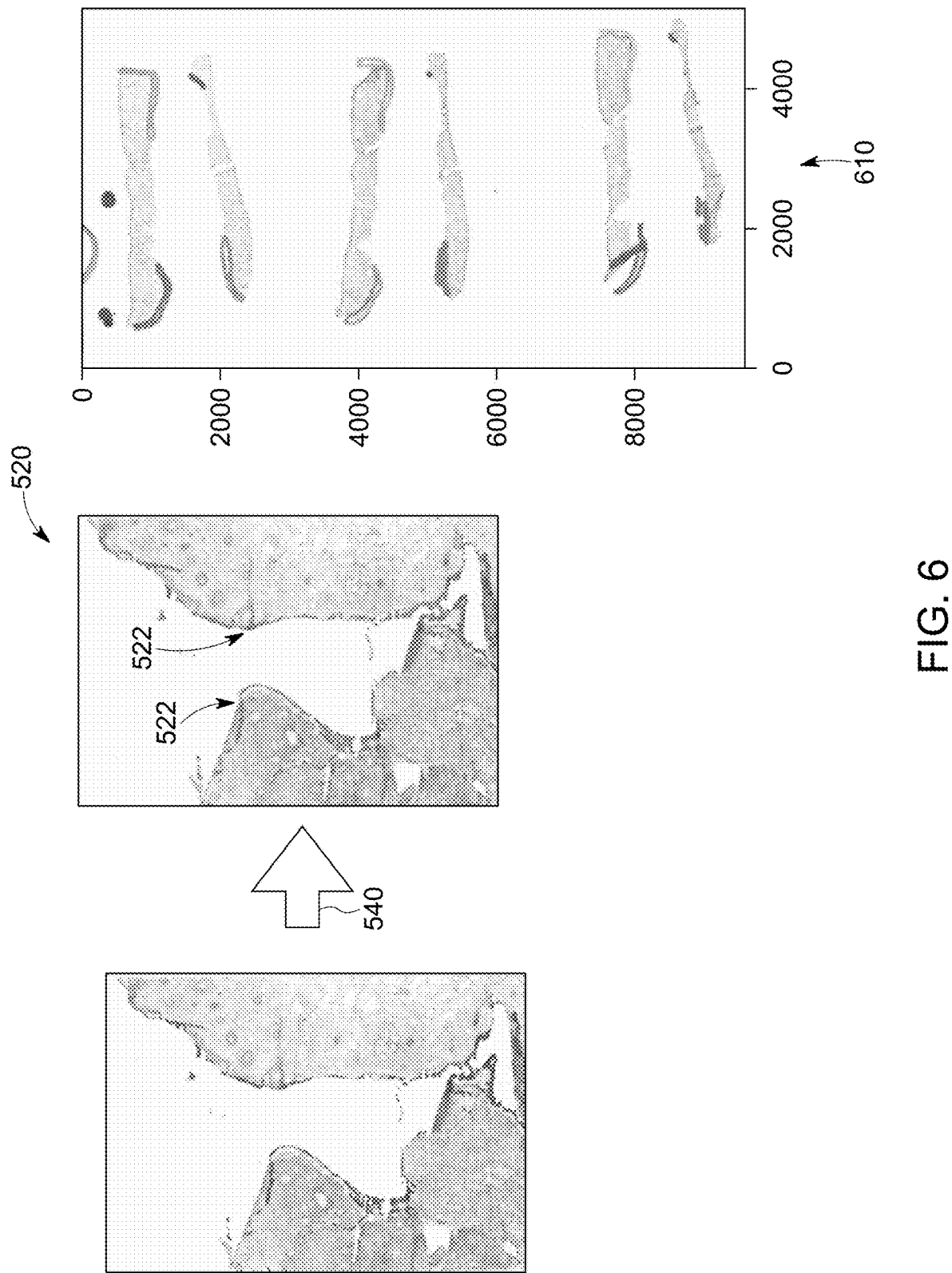
FIG. 6 is a diagram showing exemplary images and results associated with automated ink detection system associated with FIG. 5.

The system and method includes a process that determines the ink color scheme for a piece of tissue 510 that has been surgically removed. The system and method thereby defines the grossing and inking scheme (procedure 200) based on the size, shape of the tissue, and % of margin desired to be analyzed. The tissue is then inked 512 accordingly (See the process 500 of FIG. 5). Slides are created and scanned resulting in digital whole slide images (WSI) 520 (See also FIG. 6). The system and method further provides an automated digital ink identification system that selectively identifies the location and color of ink on the edges 522 of a piece of tissue. The ink detection system is based on color thresholding in the HSV space and a series of morphometric operations—for example, Sobel and gradient-based filters can operate (arrow 540) to find the tissue edge 522; and a series of binary opening, closing and nearest-neighbor labeling operations, followed by removal of small connected components) that extract ink only on the edge of the tissue. It is notable that the process is capable of automatically estimating the orientation, placement and depth of the tissue section based on series of spatial statistics (See box 610 showing the results of the system and method's automated ink detection system) that are calculated on the locations of ink colors including but not limited to: red, yellow, green, blue, black, orange and purple inks (512) for each tissue section in accordance with best practices.

3. Use of Convolutional/Graph Neural Networks to Assess Slide Quality

Slide quality is assessed by the system and method by identifying tissue artifacts, tears and holes which may cause the surgical pathologist to unknowingly miss diagnostically important regions of tissue, weighted by both their prognostic significance and contextualized by information presented in adjacent sections (3D). First, tissue is detected using a combination of advanced filtration techniques/morphometric operations, which also serves to identify and flag potential holes and tears in the tissue. Since these areas of low intensity imaging can be confused with regions of fat, wispy dermis, edema, cystic cavities or lumina, the computing procedure separately applies a set of deep learning algorithms to distinguish these holes from other possible conflating regions by informing prediction from contextual cues in the surrounding tissue macroarchitecture.

Figure 7:
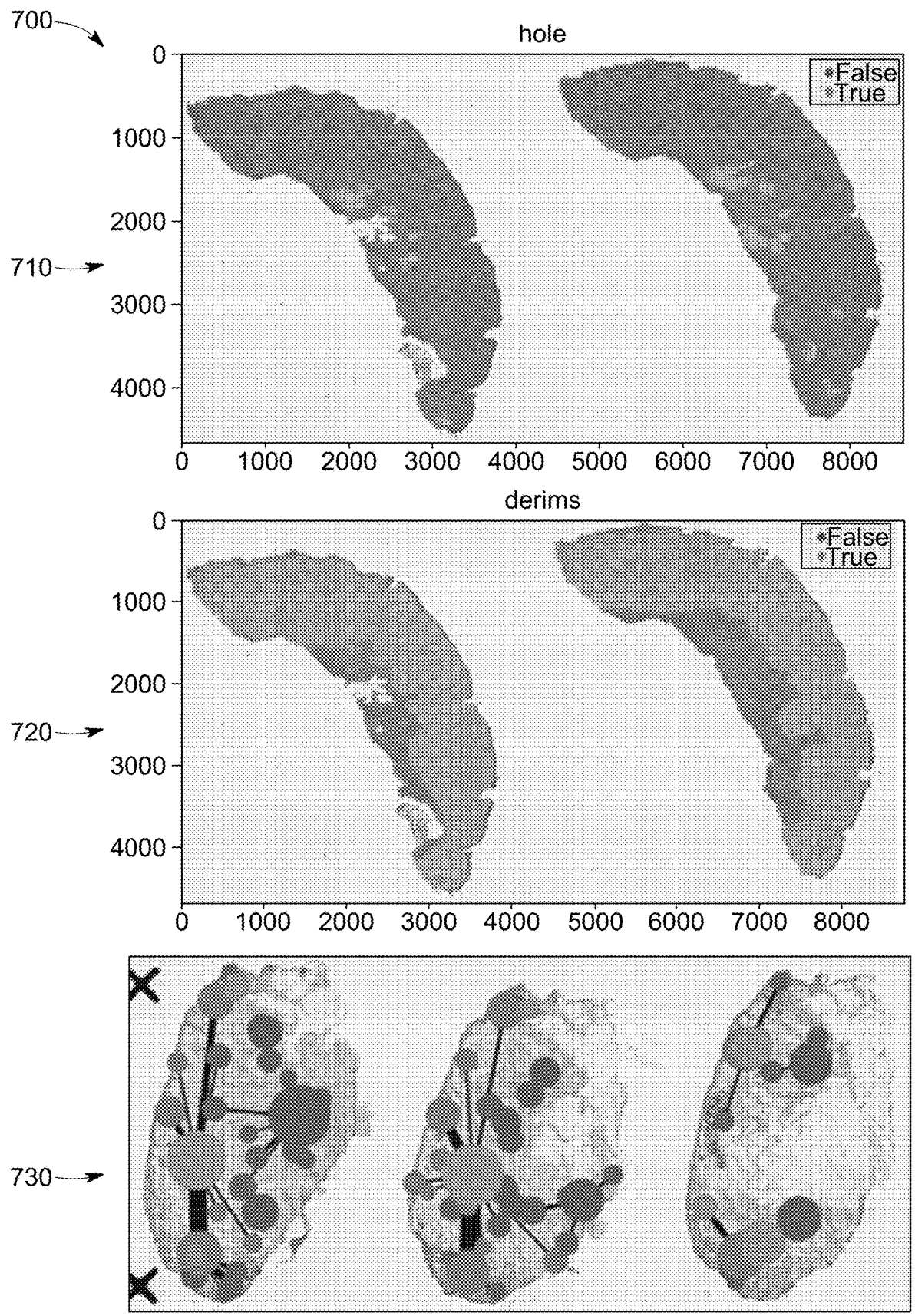
FIG. 7 is a diagram showing exemplary images associated with results of an artifact finding process and connection of holes to adjacent subregions using TDA.
Figure 8:
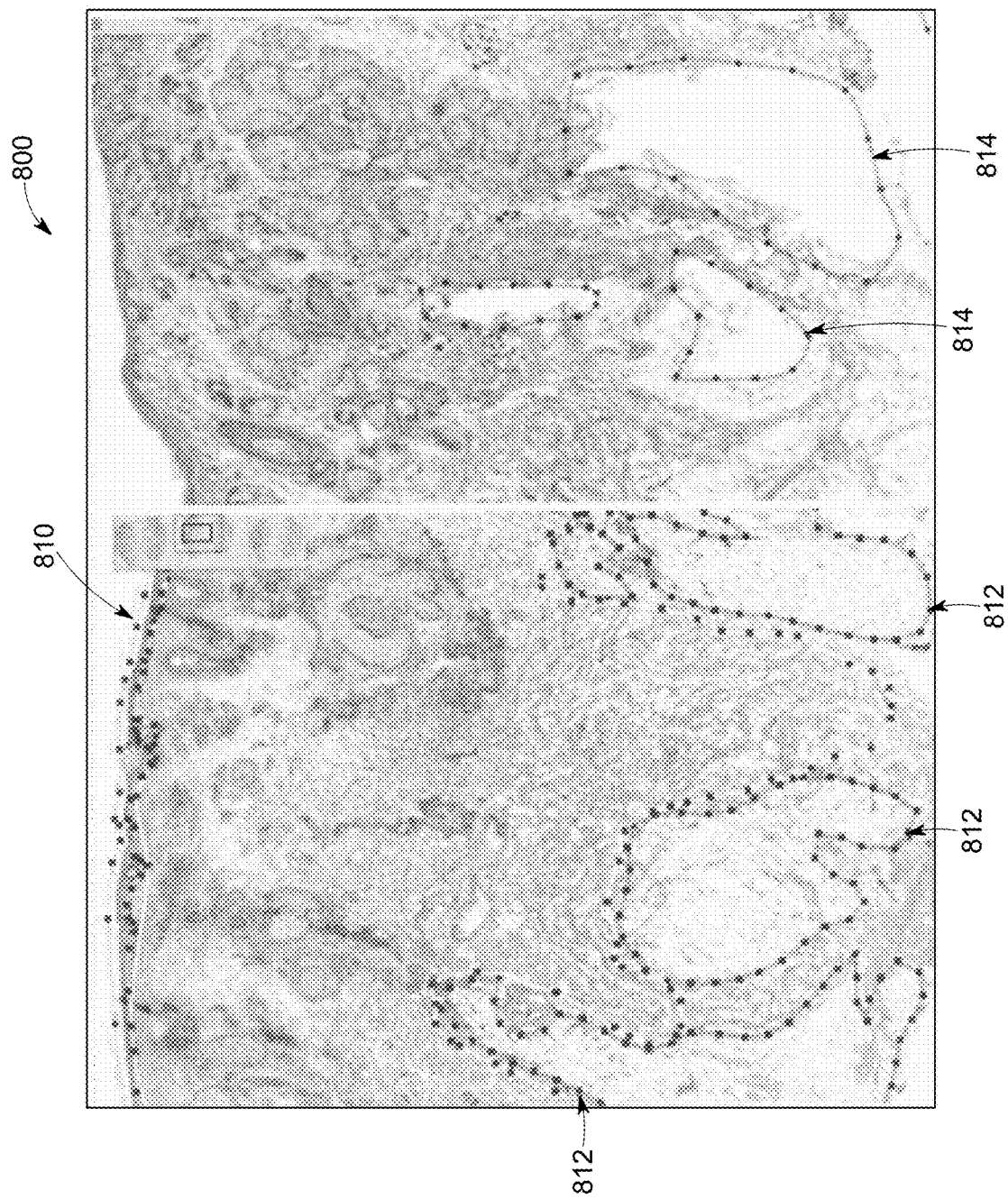
FIG. 8 is a diagram showing WSI annotated images to define appropriate tissue layers or components and areas missing.

With reference to the color imagery diagram 700 of FIG. 7, the system and method applies two separate Convolutional Neural Network/Graph Neural Network (CNN/GNN) models to: (a) label fat and holes 710, dermis and epidermis 720, and tumor regions and (b) predict the presence of malignant tumor and differentiate it from benign and inflammatory tissue. Expert annotations from whole slide images (WSIs) contribute development/training of the CNN/GNN models used by the system and method. Reference is made to the images 800 of FIG. 8, in which WSI annotation 810, 812 and 814 (each defining a differing color) is used to define appropriate tissue layers or components and areas missing.

Figure 9:
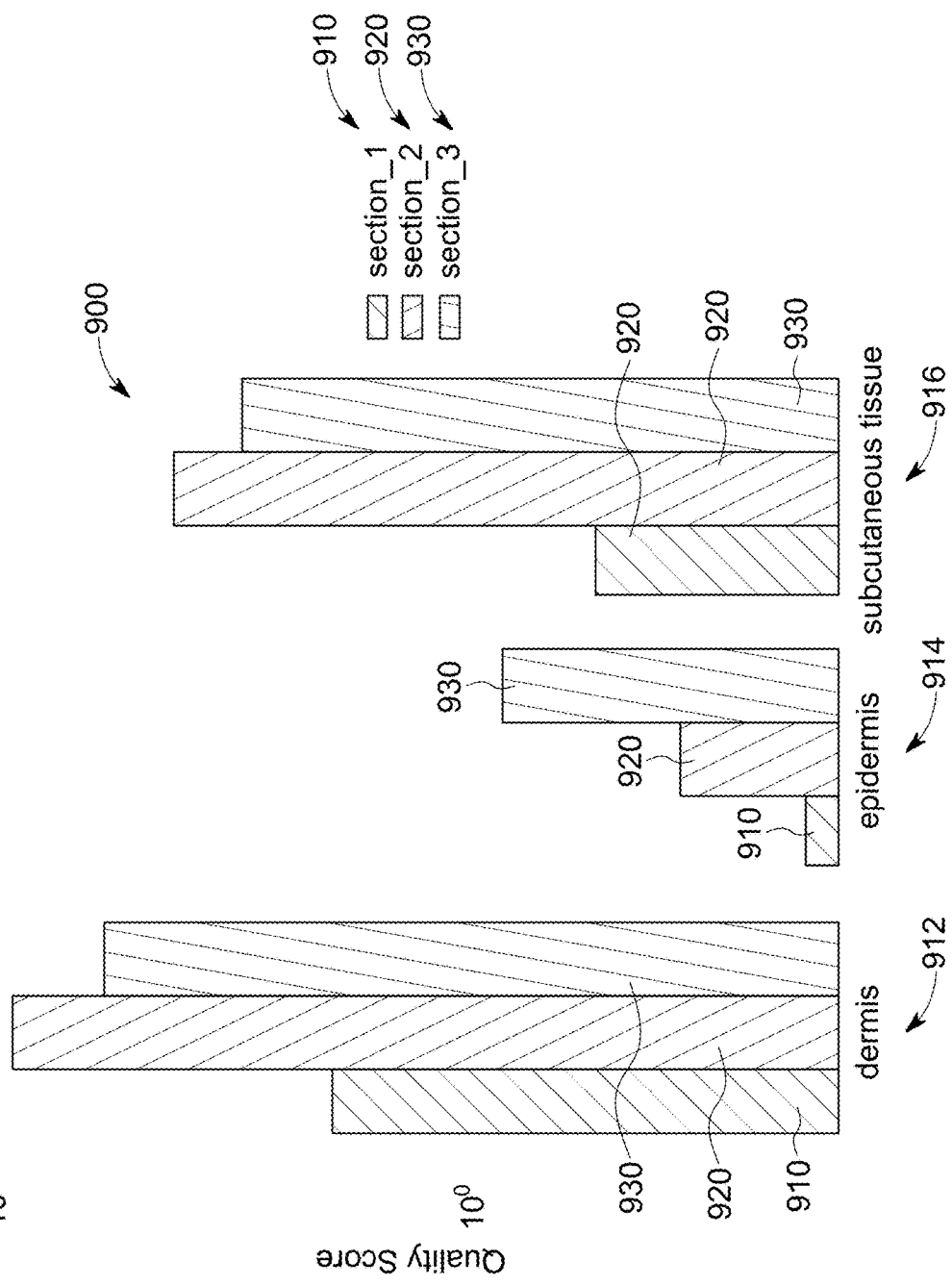
FIG. 9 is an exemplary bar graph showing slide quality score based upon the processes of the system and method.

With predictions produced by the system and method, persistence homology and Mapper subroutines from topological data analysis are used to both (a) process the shape of the tissue for overall metrics of missing tissue and (b) develop/generate a score for each section for how much the tissue artifacts intermingle into prognostically important regions of tissue (See box 730 in FIG. 7 and the graph 900 of FIG. 9). By way of example, the graph divides the results (bars) into three sections 910 920 and 930 and based upon dermis 902, epidermis 914 and subcutaneous tissue 916. In this example, the score is logarithmically presented between 0 and 10. The hole quality score 952 and tumor quality score 954 are each depicted numerically in the printout 950 of FIG. 9A. After calculating the intermingling between the artifacts, tumor, fat, squamous regions, epidermis and dermis regions, the amount of intermingling of both holes and tumors with these tissue regions in serial sections or levels of the same tissue are compared stereotactically to capture the importance of missing a hole in the current section as a function of the quality and malignancy of its neighboring sections incorporating three dimensional information.

The system and method can employ Topological Data Analysis (TDA) so as to reveal key relationships in the data (in this case, morphological and spatial information encoded in each of the WSI subimages) by collapsing irrelevant structures and predicting how tissue is expected to be distributed versus what is observed. The Mapper process/algorithm, a smart TDA clustering technique, decomposes the WSI into overlapping Regions of Interest (ROI) that are representative of different tissue subcompartments, and forms weighted connections between ROIs to portray shared information content and important functional relationships. The system and method applies these processes/algorithms to calculate the intermingling of the hole with the surrounding tissue architecture for where artifacts are located in the slide with respect to important architectural components (importance assignment). The system and method further uses area calculations for quantitating total amount of holes (amount of bad quality), and compares TDA measurements across sections for assess the likelihood of a tumor being where the hole is in the current section (importance assignment; e.g. if hole in dermis of present section but adjacent section contains tumor in dermis). The quality of a particular tissue may be assessed given the following mathematical relationship:

$$\text{Quality}_{section\ i} = \sum_{region \in \{fat, dermis, \ldots\}} \text{importance}_{region} * \left( \text{holes}_{region} + \sum_{j \in \{0,1,2,\ldots\}} \text{tumor}_{region, section\ j} * [\lambda * \text{distance}_{section\ i, section\ j}]^{-1} \right)$$

Where the importance of each region and the weight given to adjacent sections at a particular distance is determined via expert knowledge. Note these approaches can be applied to any tissue type assuming CNN/GNN trained on expert truth and/or on specialized staining patterns.

5. Operational Procedure of a Digital Pathology System

Figure 10:
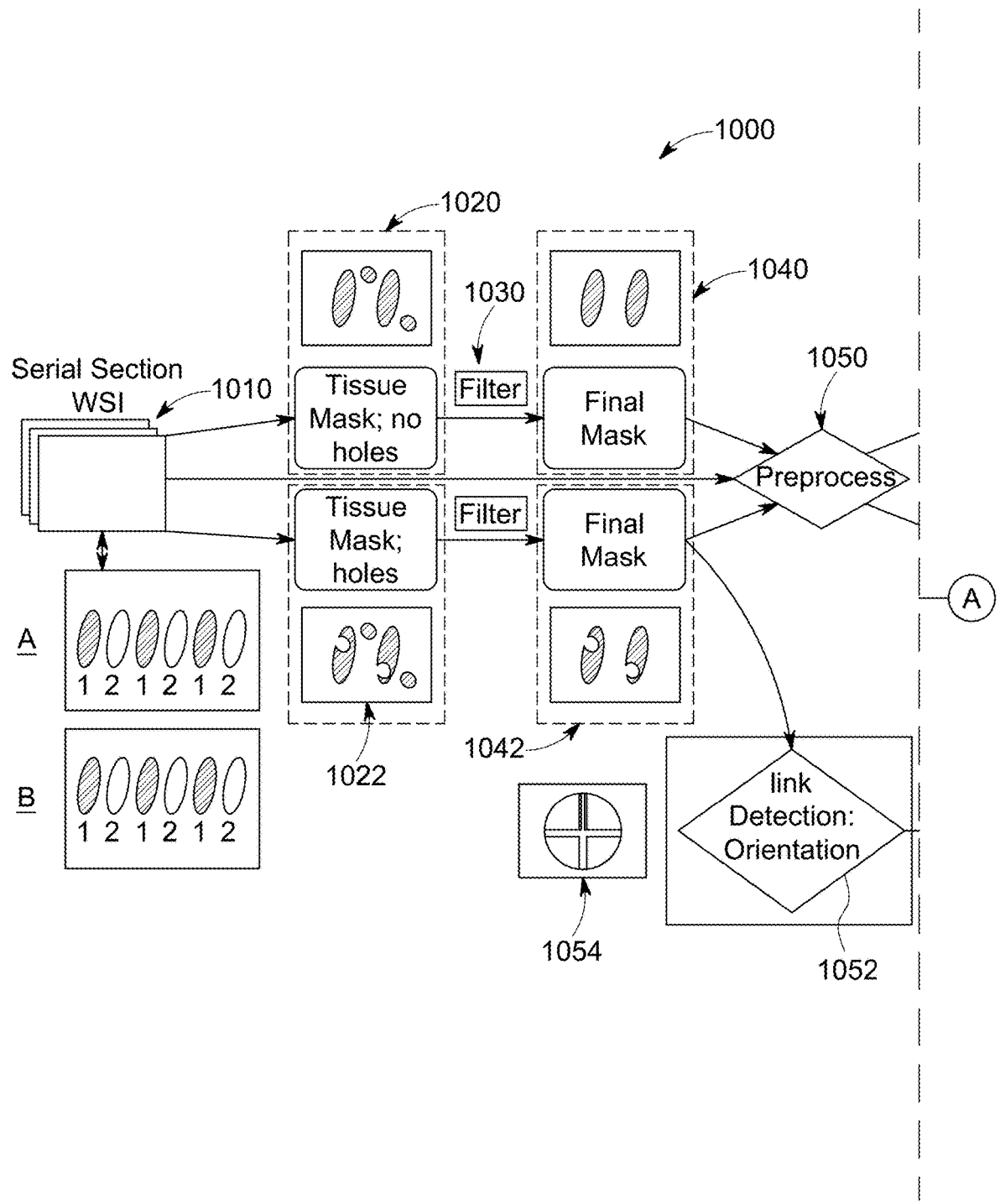
FIG. 10 (and FIG. 10 (Continued)) is a flow diagram showing the operation of quality/ink assessments and automated report generation in a digital pathology ecosystem according to the system and method.
Figure 10:
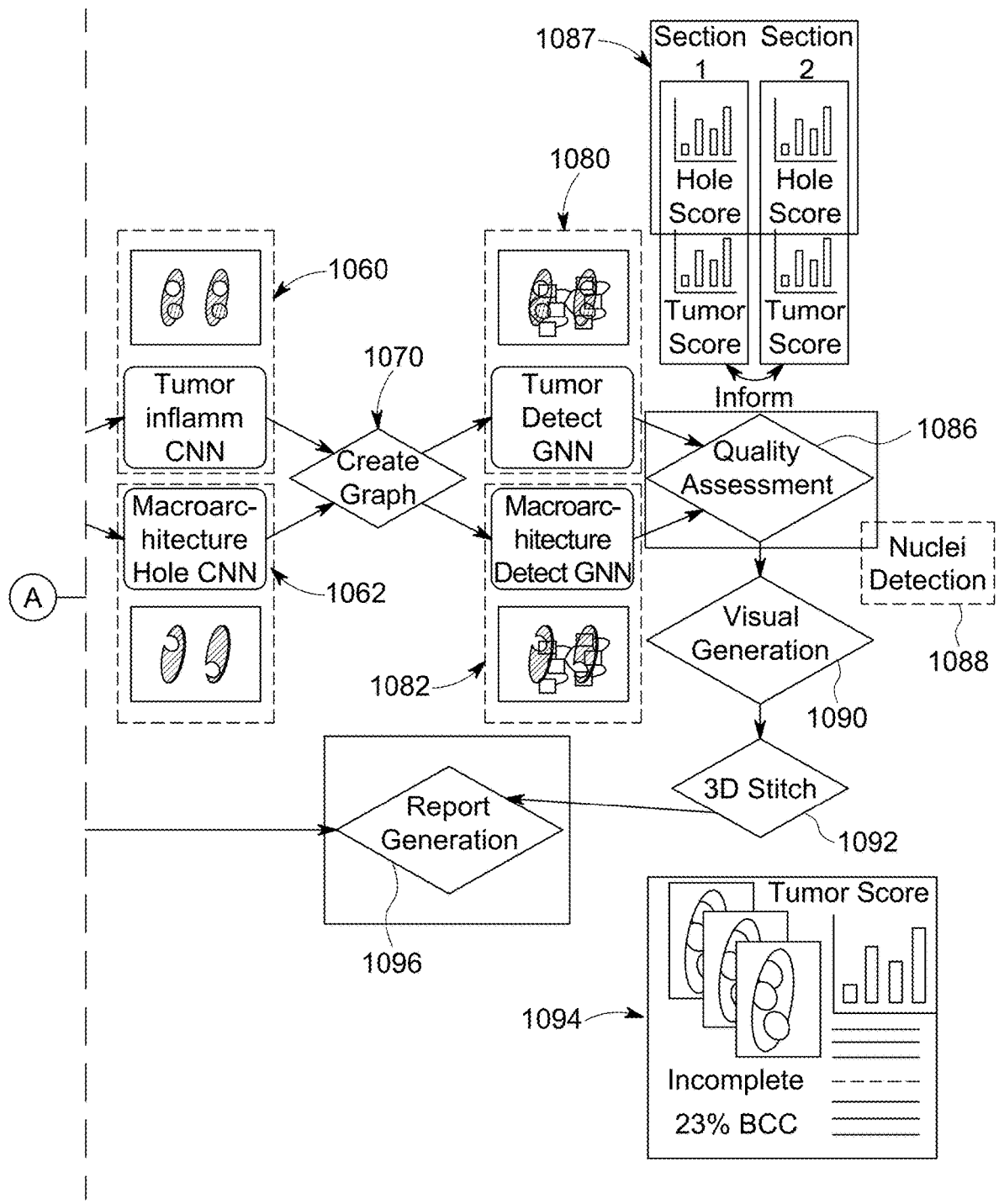

Reference is made to FIG. 10 (which is continued at branch A on a second sheet), which shows the generalized operation of an automated pathology procedure 1000 according to an illustrative embodiment. The procedure 1000 provides serial section WSIs 1010 that can define various sections (1 and 2) in exemplary slides (A and B). The inked/segmented images in the slides are scanned and divided into images based upon tissue masks, so as to provide results with no holes 1020 and results with holes 1022. These images 1020, 1022 are provided to a filtering process 1030 to derive a final masked image for no holes 1040 and holes 1042. Both image results are delivered to a preprocess step 1050 and the final mask results for holes 1042 is also generated and provided to the ink detection and orientation process 1052, which is represented by oriented image 1054. The preprocess step 1050 delivers results to a trained tumor inflammation CNN 1060 and a macroarchitecture hole CNN 1062. These CNNs thereby provide results to a graphical creation step 1070. This step delivers results to a tumor detection GNN 1080 and macroachitecture detection GNN 1082, which, in turn provides results to a quality assessment step 1086. This allows generation of score graphs 1087 for each section (e.g. 1 and 2) as also shown in FIG. 9. A nuclei detection sub-process 1088 is applied to the results and can be used in conjunction with a visual generation step 1090, which provides results to a 3D stitching step 1092. The results of the steps 1090 and 1092 are used to provide report displays 1094 as part of report generation (step 1096). Such report generation can also include use of results from the above-described ink detection and orientation process 1052, as shown.

6. Conclusion

It should be clear that the above-described system and method provides an effective and useful tool for automating the overall pathology process for a range of WSI samples. It provides the practitioner with objectively scored results that assist in making further determinations relative to diagnosis of conditions, such as cancer. The techniques herein can be refined continuously by further training of applicable AI algorithms and can be applied to an increasing range of medical conditions and parts of the body. Results can be delivered in a manner that provides revenue to the system operators, and can be delivered to any region or device via existing communications networks, including highly remote areas that may lack sophisticated equipment or facilities.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, the use of various colors and color-codings in images is exemplary of a wide range of possible indicia for distinguishing between characteristics in a display or physical structure. Grayscale shading and/or use of non-visible wavelengths, or other characteristics, can be used to distinguish such items, in a manner clear to those of skill. Also, as used herein, various directional and orientational terms (and grammatical variations thereof) such as "vertical", "horizontal", "up", "down", "bottom", "top", "side", "front", "rear", "left", "right", "forward", "rearward", and the like, are used only as relative conventions and not as absolute orientations with respect to a fixed coordinate system, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Note also, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub-processors can be variously combined according to embodiments herein. Accordingly, this description is meant to be taken only by way of example, and not to otherwise limit the scope of this invention.

What is claimed is:

1. A system for automation of a pathology process comprising;
    a processor having a neural network, having trained artificial intelligence (AI) modules operating in association therewith, adapted to receive image data from images of whole tissue acquired by an camera assembly and whole slide images (WSIs) of inked and segmented tissue samples;
    a mask that produces image results for tissue with holes and free of holes;
    a filter that provides filtered image results to the AI modules, which thereby detects tumors and macroarchitecture features;
    a quality assessment process that produces quality score outputs for tumors and macroarchitecture features;
    a report generator that provides reports with one or more parameters to a user via an interface;
    a tissue determination process that determines a size and a description of tissue automatically based upon characteristics in the images acquired by the camera assembly;
    a tissue grossing and inking process that automatically generates a grossing and inking scheme based upon a user input of desired percentage of tissue margins analyzed and the tissue size; and
    an ink detection and orientation process that operates on the filtered images of the tissue samples and delivers results thereof to the report generator, and
    wherein the macroarchitecture features are defined by holes, fat, edges, dermis and epidermis information.

2. The system as set forth in claim 1 wherein the AI modules include a tumor inflammation convolutional neural network (CNN), a macroarchitecture hole CNN, a tumor detection graphical neural network (GNN) and a macroarchitecture detection GNN.

3. The system as set forth in claim 1 wherein the report generator receives results from the quality assessment process, and wherein the quality assessment process acts on results from a tumor detection GNN and a macroarchitecture detection GNN.

4. The system as set forth in claim 1, further comprising, a visual generation and 3D stitching process that provides results to the report generator.

5. The system as set forth in claim 1, wherein the report generator automatically creates a pathology report consisting of a written description and pictorial diagram relative to the images of the tissue.

6. The system as set forth in claim 2 wherein the filters include at least one of a Sobel filter and a gradient-based filter.

7. The system as set forth in claim 3 wherein the report generator automatically creates a pathology report consisting of a written description and pictorial diagram relative to the images of the tissue.

8. The system as set forth in claim 4 wherein the visual generation process receives information from a cell nuclei detection process.

9. The system as set forth in claim 8 wherein the report generator automatically creates a pathology report consisting of a written description and pictorial diagram relative to the images of the tissue.

10. A method for automation of a pathology process comprising the steps of:
    providing a processor with a neural network having artificial intelligence (AI) modules operating in association therewith, which receive image data from camera images of whole tissue acquired by an camera assembly and whole slide images (WSIs) of inked and segmented tissue samples;
    producing image results for tissue with holes and free of holes with a mask;
    providing filtered image results to the AI modules, and detecting tumors and macroarchitecture features therewith;
    generating quality score outputs for tumors and macroarchitecture features;
    generating a report with one or more parameters to a user via an interface;
    determining a size and a description of tissue automatically based upon characteristics in the images acquired by the camera assembly;
    automatically generating a grossing and inking scheme based upon a user input of desired percentage of tissue margins analyzed and the tissue size; and
    operating an ink detection and orientation process on the filtered images of the tissue samples that delivers results thereof to the report generator, and
    wherein the macroarchitecture features are defined by holes, fat, edges, dermis and epidermis information.

11. The method as set forth in claim 10, wherein the step of generating the report includes automatically creating a pathology report consisting of a written description and pictorial diagram relative to the images of the tissue.

12. The system as set forth in claim 10, further comprising, defining the AI modules to include a tumor inflammation convolutional neural network (CNN), a macroarchitecture hole CNN, a tumor detection graphical neural network (GNN) and a macroarchitecture detection GNN.

13. The method as set forth in claim 10, further comprising, wherein the step of generating includes receiving results from a quality assessment process acting on results from a tumor detection GNN and a macroarchitecture detection GNN.

14. The method as set forth in claim 10, further comprising, wherein the step of generating includes operating a visual generation and 3D stitching process that provides results.

15. The method as set forth in claim 12, wherein the step of providing filtered image results includes operating at least one of a Sobel filter and a gradient-based filter.

16. The method as set forth in claim 14, further comprising, receiving by the visual generation process, information from a cell nuclei detection process.

17. The method as set forth in claim 16, wherein the step of generating the report includes automatically creating a pathology report consisting of a written description and pictorial diagram relative to the images of the tissue.

\* \* \* \* \*